US008530705B2

(12) United States Patent
Nishimura et al.

(10) Patent No.: US 8,530,705 B2
(45) Date of Patent: Sep. 10, 2013

(54) PURIFICATION METHOD OF DIHYDROXYBENZENE

(75) Inventors: Mayumi Nishimura, Toyota (JP); Shigeru Goto, Chiba (JP); Tomoyuki Noritake, Ichihara (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 128 days.

(21) Appl. No.: 13/258,257

(22) PCT Filed: Mar. 24, 2010

(86) PCT No.: PCT/JP2010/055780
§ 371 (c)(1),
(2), (4) Date: Sep. 21, 2011

(87) PCT Pub. No.: WO2010/110482
PCT Pub. Date: Sep. 30, 2010

(65) Prior Publication Data
US 2012/0022297 A1      Jan. 26, 2012

(30) Foreign Application Priority Data

Mar. 25, 2009 (JP) .................. 2009-073722

(51) Int. Cl.
*C07C 37/68* (2006.01)
*C07C 37/72* (2006.01)
*C07C 37/74* (2006.01)
*C07C 37/08* (2006.01)

(52) U.S. Cl.
USPC .......................................... 568/753; 568/798

(58) Field of Classification Search
USPC ............................................ 568/753
See application file for complete search history.

(56) References Cited

U.S. PATENT DOCUMENTS

| 2,381,209 | A | * | 8/1945 | Cotton ........................ 568/753 |
| 3,968,171 | A | * | 7/1976 | Burkholder et al. .......... 568/753 |
| 6,423,876 | B1 | | 7/2002 | Tokumasu |

FOREIGN PATENT DOCUMENTS

| JP | 53-053626 A | 5/1978 |
| JP | 60-239430 A | 11/1985 |
| JP | 64-000038 A | 1/1989 |
| JP | 2002-363118 A | 12/2002 |

* cited by examiner

Primary Examiner — Brian J Davis
(74) Attorney, Agent, or Firm — Sughrue Mion, PLLC (57) ABSTRACT

A purification method of dihydroxybenzene comprising the following steps, for obtaining purified dihydroxybenzene from crude dihydroxybenzene containing at least isopropenylphenol and hydroxyacetophenone as impurities: first extraction step, distillation step, second extraction step, and recovery step.

8 Claims, 5 Drawing Sheets

PURIFICATION METHOD OF DIHYDROXYBENZENE

CROSS REFERENCE TO RELATED APPLICATION

This application is a National Stage of International Application No. PCT/JP2010/055780 filed Mar. 24, 2010, claiming priority based on Japanese Patent Application No. 2009-073722, filed Mar. 25, 2009, the contents of all of which are incorporated herein by reference in their entirety.

TECHNICAL FIELD

The present invention relates to a purification method of dihydroxybenzene. More particularly, the present invention relates to a purification method of dihydroxybenzene, which is capable of efficiently obtaining highly purified dihydroxybenzene.

BACKGROUND ART

As a method for industrially producing dihydroxybenzene typified by resorcin, there is known a method in which benzene and propylene are reacted to obtain diisopropylbenzene, the diisopropylbenzene is oxidized to give diisopropylbenzene hydroperoxide, and the diisopropylbenzene hydroperoxide is acid-decomposed to give dihydroxybenzene and acetone (see, e.g., patent document 1).

Here, dihydroxybenzene obtained by the above-described method is crude dihydroxybenzene containing isopropenylphenol, hydroxyacetophenone and the like as impurities. Thus, it is necessary to perform purification by removing the above-described impurities and the like from the crude dihydroxybenzene, for obtaining dihydroxybenzene as a product.

It is also known that dihydroxybenzene is required to have high level product purity depending on applications and a purification method for obtaining highly purified dihydroxybenzene has been developed (see, e.g., patent document 2).

As a method for purifying crude dihydroxybenzene, methods of adding water and an extraction solvent to crude dihydroxybenzene and extracting dihydroxybenzene into an aqueous phase are described in patent document 3 and patent document 4.

However, there is a desire for methods of efficiently obtaining dihydroxybenzene which is more highly purified than in conventional methods.
(Patent document 1) JP-A No. 53-23939
(Patent document 2) JP-B No. 61-18537
(Patent document 3) JP-A No. 64-38
(Patent document 4) JP-A No. 2002-363118

DISCLOSURE OF THE INVENTION

Under such circumstances, the problem to be solved by the invention is to provide a purification method of dihydroxybenzene, which is capable of efficiently obtaining highly purified dihydroxybenzene.

That is, the present invention relates to a purification method of dihydroxybenzene comprising the following steps, for obtaining purified dihydroxybenzene from crude dihydroxybenzene containing at least isopropenylphenol and hydroxyacetophenone as impurities:

first extraction step: water is added to crude dihydroxybenzene to prepare a dihydroxybenzene aqueous solution A, then, the solution is subjected to extraction by allowing it to contact with an extraction solvent (1), to be separated into a first fraction containing dihydroxybenzene, hydroxyacetophenone and water and a second fraction containing isopropenylphenol and the extraction solvent (1), distillation step: the first fraction obtained in the first extraction step is subjected to distillation, to be separated into a third fraction containing water and a fourth fraction containing dihydroxybenzene and hydroxyacetophenone, then, the fourth fraction is subjected to distillation, to be separated into a fifth fraction as purified dihydroxybenzene and a sixth fraction as dihydroxybenzene containing concentrated hydroxyacetophenone, second extraction step: water is added to the sixth fraction obtained in the distillation step to prepare a dihydroxybenzene aqueous solution B, then, the solution is subjected to extraction by allowing it to contact with an extraction solvent (2), to be separated into a seventh fraction containing dihydroxybenzene and water and an eighth fraction containing hydroxyacetophenone and the extraction solvent (2), recovery step: dihydroxybenzene is recovered from the seventh fraction obtained in the second extraction step or the seventh fraction obtained in the second extraction step is fed to the entrance of the first extraction step.

Further, the present invention relates to a production method of dihydroxybenzene comprising the following steps wherein the following purification step uses the above-described purification method of dihydroxybenzene:

oxidation step: diisopropylbenzene is oxidized to obtain an oxidized oil containing diisopropylbenzene dihydroperoxide, decomposition step: the oxidized oil obtained in the oxidation step is decomposed in the presence of an acidic catalyst to obtain a decomposition reaction solution containing dihydroxybenzene, purification step: the decomposition reaction solution obtained in the decomposition step is purified to obtain purified dihydroxybenzene.

DESCRIPTION OF NUMERALS (1) crude dihydroxybenzene (crude resorcin)
(2) water
(3) resorcin aqueous solution A
(4) extraction solvent (1)
(5) first fraction
(6) second fraction
(7) third fraction
(8) fourth fraction
(9) fifth fraction
(10) sixth fraction
(11) water
(12) resorcin aqueous solution B
(13) extraction solvent (2)
(14) seventh fraction
(15) eighth fraction
(16) ninth fraction
(17) tenth fraction (18) dihydroxybenzene to be recovered
(101) extraction tower in first extraction step
(102) distillation tower for former distillation of distillation step
(103) distillation tower for latter distillation of distillation step
(104) extraction tower in second extraction step
(105) distillation tower for former distillation of recovery step
(106) distillation tower for latter distillation of recovery step Modes for Carrying Out the Invention Embodiments of the present invention will be illustrated in detail below.

The purification method of hydroxybenzene of the present invention is a purification method for obtaining purified dihydroxybenzene from crude dihydroxybenzene containing at least isopropenylphenol and hydroxyacetophenone as impurities, the method comprising the following steps:

first extraction step: water is added to crude dihydroxybenzene to prepare a dihydroxybenzene aqueous solution A, then, the solution is subjected to extraction by allowing it to contact with an extraction solvent (1), to be separated into a first fraction containing dihydroxybenzene, hydroxyacetophenone and water and a second fraction containing isopropenylphenol and the extraction solvent (1), distillation step: the first fraction obtained in the first extraction step is subjected to distillation, to be separated into a third fraction containing water and a fourth fraction containing dihydroxybenzene and hydroxyacetophenone, then, the fourth fraction is subjected to distillation, to be separated into a fifth fraction as purified dihydroxybenzene and a sixth fraction as dihydroxybenzene containing concentrated hydroxyacetophenone, second extraction step: water is added to the sixth fraction obtained in the distillation step to prepare a dihydroxybenzene aqueous solution B, then, the solution is subjected to extraction by allowing it to contact with an extraction solvent (2), to be separated into a seventh fraction containing dihydroxybenzene and water and an eighth fraction containing hydroxyacetophenone and the extraction solvent (2), recovery step: dihydroxybenzene is recovered from the seventh fraction obtained in the second extraction step or the seventh fraction obtained in the second extraction step is fed to the entrance of the first extraction step.

The crude hydroxybenzene in the present invention contains at least isopropenylphenol and hydroxyacetophenone as impurities. As the impurity, other impurities than isopropenylphenol and hydroxyacetophenone may also be contained.

The concentration of isopropenylphenol in crude dihydroxybenzene is preferably 0.1 to 20 wt %, and the concentration of hydroxyacetophenone in crude dihydroxybenzene is preferably 0.1 to 10 wt %.

As the method of obtaining crude dihydroxybenzene in the present invention, there is, for example, a method in which benzene and propylene are reacted to obtain diisopropylbenzene, the diisopropylbenzene is oxidized to give diisopropylbenzene hydroperoxide, and the diisopropylbenzene hydroperoxide is acid-decomposed to give dihydroxybenzene and acetone (see, e.g., the above-described patent document 1).

The dihydroxybenzene includes, for example, resorcin, hydroquinone, catechol and the like, and from the standpoint of industrial importance, resorcin is preferable. Resorcin is principally used as a main raw material of an adhesive.

The first extraction step in the present invention is a step in which water is added to crude dihydroxybenzene to prepare a dihydroxybenzene aqueous solution A, then, the solution is subjected to extraction by allowing it to contact with an extraction solvent (1), to be separated into a first fraction containing dihydroxybenzene, hydroxyacetophenone and water and a second fraction containing isopropenylphenol and the extraction solvent (1).

The concentration ($C_A$) of dihydroxybenzene in the aqueous solution A obtained by adding water to crude dihydroxybenzene is preferably 40 to 70 wt %, more preferably 40 to 60 wt %. When the concentration is too low (namely, when the ratio of water with respect to dihydroxybenzene is high), the quantity of heating energy used for separation into a third fraction containing water and a fourth fraction containing dihydroxybenzene and hydroxyacetophenone in the distillation step as the latter step is required to be large, and a large scale distillation tower is necessary in this step, leading to poor economy, while when the concentration is too high (namely, when the ratio of water with respect to dihydroxybenzene is low), the ability of removing isopropenylphenol and hydroxyacetophenone in the extraction step lowers, causing deterioration of purification efficiency, and if the solution temperature lowers, dihydroxybenzene in the solution deposits, inducing troubles such as piping blockage and the like in some cases, for example, in the case of lowering of external temperature.

As the extraction solvent (1), suitable solvents can be selected by the operator from known extraction solvents. Examples of the extraction solvent (1) include toluene, xylene, cymene, triisopropylbenzene, diisopropylbenzene and the like, and from the standpoint of extraction efficiency and liquid separation performance, toluene is preferable. For enhancing extraction efficiency, a mixed extraction solvent obtained by additionally mixing ketones in addition to the above-described extraction solvent (1) may also be used. As the ketones to be mixed, acetone, methyl ethyl ketone, methyl isobutyl ketone and the like are listed, and of them, methyl isobutyl ketone is preferable.

The specific extraction methods include methods of extraction using a known extraction tower, for example, a method in which a solution composed of crude dihydroxybenzene and water is fed from a position near the tower head of an extraction tower and an extraction solvent is fed from a position near the tower bottom and both solutions are allowed to contact in counter-current fashion and be extracted in an extraction tower, and other methods. The extraction tower may have given extraction theoretical stages, and examples thereof include a porous plate extraction tower having a porous plate placed inside, a baffle tower having a baffle plate, a RDC tower equipped with a rotating disc, and the like.

Examples of other extraction methods include a method of extraction using a mixer settler mode in which a solution composed of crude dihydroxybenzene and water, and an extraction solvent are allowed to contact and be mixed using a contact mixing apparatus (mixer), then, oil-water separation is performed; and other methods. Examples of the contact mixing apparatus (mixer) include commercially available general mixing apparatuses such as a stirrer, static mixer, line mixer and the like. In the mixer settler mode after contact mixing, an oil-water separation apparatus (settler) can be used, and the oil-water separation apparatus (settler) may advantageously be one in which oil and water are sufficiently allowed to stand still and be separated, and examples thereof include general drums, coalescers and the like.

By extraction, a first fraction containing dihydroxybenzene, hydroxyacetophenone and water and a second fraction containing isopropenylphenol and the extraction solvent (1) are obtained. In the case of use of the above-described extraction tower, the first fraction is obtained from around the tower bottom of an extraction tower, and the second fraction is obtained from around the tower head of an extraction tower.

In contrast, in the case of use of a mixer settler, the first fraction is obtained from the aqueous phase side of a settler, and the second fraction is obtained from the oil phase side of a settler.

Regarding the concentrations of dihydroxybenzene and hydroxyacetophenone contained in the first fraction, it is preferable that the concentration of dihydroxybenzene is 40 to 70 wt % and the concentration of hydroxyacetophenone is 0.05 to 0.4 wt % (here, the total weight of the first fraction is 100 wt %). The concentration of isopropenylphenol contained in the second fraction is preferably 0.05 to 5.0 wt % (here, the total weight of the second fraction is 100 wt %).

Since the second fraction contains the extraction solvent (1), it may be used as it is as the extraction solvent (2) in the second extraction step, alternatively, it may be subjected to distillation, the purified extraction solvent may be recovered, and recycled and used as the extraction solvent (1) and/or extraction solvent (2) in the first and/or second extraction step.

The distillation step in the present invention is a step in which the first fraction obtained in the first extraction step is subjected to distillation, to be separated into a third fraction containing water and a fourth fraction containing dihydroxybenzene and hydroxyacetophenone, then, the fourth fraction is subjected to distillation, to be separated into a fifth fraction as purified dihydroxybenzene and a sixth fraction as dihydroxybenzene containing concentrated hydroxyacetophenone.

For carrying out the distillation step, known distillation towers such as a tray tower, irregular packed tower and regular packed tower are used. As the main constitutions of the distillation tower, exemplified are those composed of a distillation tower body having internal structures such as trays (sieve tray, ripple tray, bubble cap tray and the like), irregular fillers (rasching ring, lessing ring, pall ring and the like) and regular fillers (mellapak and the like) installed therein singly or in combination of two or more, a reboiler for partially vaporizing a solution near the tower bottom, and a condenser for condensing the distilled vapor near the tower head. Several such distillation towers are placed if necessary, and desired fractions are extracted from a position near the tower heat, a position near the tower bottom, or a position near the intermediate stage between the tower head and the tower bottom, called a side cut, thereby carrying out separation thereof. Specifically, a third fraction containing water is obtained from around the tower heat of the distillation tower of the former stage, a fourth fraction containing dihydroxybenzene and hydroxyacetophenone is obtained from around the tower bottom, then, the fourth fraction is subjected to distillation in the distillation tower in the latter stage, and a fifth fraction as purified dihydroxybenzene is obtained from around the tower head of the distillation tower and a sixth fraction as dihydroxybenzene containing concentrated hydroxyacetophenone is obtained from around the tower bottom. In the case of presence of an impurity having a boiling point lower than that of dihydroxybenzene, in dihydroxybenzene obtained around the tower head of the distillation tower of the latter stage, it is particularly preferable, from the standpoint of enhancing the purity of purified dihydroxybenzene, to obtain the fourth fraction from a stage for feeding to the distillation tower and from an intermediate stage situated near the tower head (side cut stage).

The third fraction obtained in the distillation step may be discharged out of the step, however, it may also be recycled as it is as at least a part of water used in the first extraction step and/or the second extraction step, or unnecessary components may be removed before the recycling. Recycling of the third fraction is preferable since the water discharge amount as the whole purification process of crude dihydroxybenzene is reduced.

Thus obtained fifth fraction satisfies desired qualities. The concentration of hydroxyacetophenone in the sixth fraction is usually about 5 to 12 wt %, and concentration of dihydroxybenzene in the sixth fraction is usually about 70 to 95 wt %.

The second extraction step in the present invention is a step in which water is added to the sixth fraction obtained in the distillation step to prepare a dihydroxybenzene aqueous solution B, then, the solution is subjected to extraction by allowing it to contact with an extraction solvent (2), to be separated into a seventh fraction containing dihydroxybenzene and water and an eighth fraction containing hydroxyacetophenone and the extraction solvent (2).

The sixth fraction contains heavy compounds obtained by polymerization of dihydroxybenzene and isopropenylphenol in some cases, in addition to dihydroxybenzene and hydroxyacetophenone, thus, it may be permissible to carry out a heavy cut treatment or a thermal decomposition treatment of heavy substances before addition of water.

The heavy cut treatment method includes a known distillation method.

The thermal decomposition treatment method includes a method in which a heat decomposition part by a heat exchanger and a gas-liquid separation part for recovery of the thermally decomposed product are combined, and other methods.

It is preferable that the concentration ($C_B$) of dihydroxybenzene in the dihydroxybenzene aqueous solution B obtained by adding water to the sixth fraction obtained in the distillation step in the second extraction step is lower than the concentration ($C_A$) of dihydroxybenzene of the dihydroxybenzene aqueous solution A obtained by adding water to crude dihydroxybenzene in the first extraction step, from the standpoint of an excellent hydroxyacetophenone removal ability in the second extraction step, for improving purification efficiency. That is, it is preferable to satisfy the following formula (1).

$$C_A > C_B \tag{1}$$

(wherein, $C_A$ represents the concentration [wt %] of dihydroxybenzene in the dihydroxybenzene aqueous solution A, and $C_B$ represents the concentration [wt %] of dihydroxybenzene in the dihydroxybenzene aqueous solution B).

The concentration ($C_B$) of dihydroxybenzene in the dihydroxybenzene aqueous solution B is preferably 5 to 30 wt %, more preferably 5 to 20 wt %.

As the extraction solvent (2), suitable solvents can be selected by the operator from known extraction solvents. Examples of the extraction solvent (2) include toluene, xylene, cymene, triisopropylbenzene, diisopropylbenzene and the like, and from the standpoint of extraction efficiency and liquid separation performance, toluene is preferable. The extraction solvent (1) used in the first extraction step and the extraction solvent (2) used in the second extraction step may be the same or different. For enhancing extraction efficiency, a mixed extraction solvent obtained by additionally adding particularly ketones to the above-described extraction solvent (2) may also be used. As the ketones to be added, acetone, methyl ethyl ketone, methyl isobutyl ketone and the like are listed, and of them, methyl isobutyl ketone is preferable.

As described previously, the second fraction separated in the first extraction step may be used as it is as the extraction solvent (2).

The specific extraction methods include methods of extraction using a known extraction tower, for example, a method in which a solution composed of dihydroxybenzene and water is fed from a position near the tower head of an extraction tower and an extraction solvent is fed from a position near the tower bottom and both solutions are allowed to contact in counter-current fashion and be extracted in an extraction tower, and other methods. The extraction tower may have a given extraction theoretical stages, and examples thereof include a porous plate extraction tower having a porous plate placed inside, a baffle tower having a baffle plate, a RDC tower equipped with a rotating disc, and the like.

Examples of other extraction methods include a method of extraction using a mixer settler mode in which a solution composed of crude dihydroxybenzene and water, and an extraction solvent are allowed to contact and be mixed using a contact mixing apparatus (mixer), then, oil-water separation is performed; and other methods. Examples of the contact mixing apparatus (mixer) include commercially available general mixing apparatuses such as a stirrer, static mixer, line mixer and the like. For oil-water separation after contact mixing, a known oil-water separation apparatus (settler) can be used.

The oil-water separation apparatus (settler) may advantageously be one in which oil and water are sufficiently separated, and examples thereof include general drums, coalescers and the like.

By extraction, a seventh fraction containing dihydroxybenzene and water, and an eighth fraction containing hydroxyacetophenone and the extraction solvent (2) are obtained. In the case of use of the above-described extraction tower, the seventh fraction is obtained from around the tower bottom of an extraction tower, and the eighth fraction is obtained from around the tower head of an extraction tower.

In contrast, in the case of use of a mixer settler, the seventh fraction is obtained from the aqueous phase side of a settler, and the eighth fraction is obtained from the oil phase side of a settler.

The concentration of dihydroxybenzene contained in the seventh fraction is preferably 5 to 30 wt % (here, the total weight of the seventh fraction is 100 wt %). The concentration of hydroxyacetophenone contained in the eighth fraction is preferably 0.1 to 1.0 wt % (here, the total weight of the eighth fraction is 100 wt %).

Since the eighth fraction contains the extraction solvent (2), it may be subjected to distillation to recover the extraction solvent (2), and it may be recycled and used as the extraction solvent (1) and/or extraction solvent (2) in the first and/or second extraction step.

The recovery step in the present invention is a step in which dihydroxybenzene is recovered from the seventh fraction obtained in the second extraction step or the seventh fraction obtained in the second extraction step is fed to the entrance of the first extraction step. Recovery of dihydroxybenzene means that dihydroxybenzene is purified and recovered.

The method of recovering dihydroxybenzene includes, for example, a method in which the seventh fraction is subjected to distillation, to be separated into a fraction containing water and into dihydroxybenzene, and both fractions are recovered, and other methods, and it is preferably a step in which the seventh fraction obtained in the second extraction step is subjected to distillation, to be separated into a ninth fraction containing water and a tenth fraction containing dihydroxybenzene and hydroxyacetophenone, then, the tenth fraction is subjected to distillation, and dihydroxybenzene is recovered.

In the case of carrying out recovery using distillation, known distillation towers such as a tray tower, irregular packed tower and regular packed tower are used in the distillation operation. As the main constitutions of the distillation tower, exemplified are those composed of a distillation tower body having internal structures such as trays (sieve tray, ripple tray, bubble cap tray and the like), irregular fillers (rasching ring, lessing ring, pall ring and the like) and regular fillers (mellapak and the like) installed therein singly or in combination of two or more, a reboiler for partially vaporizing a solution near the tower bottom, and a condenser for condensing the distilled vapor near the tower head.

When the composition of dihydroxybenzene does not satisfy the purity required for dihydroxybenzene, an additional distillation tower may be further installed and rectification may be carried out. By this, dihydroxybenzene contained in the seventh fraction can be recovered effectively.

The ninth fraction obtained in the recovery step may be discharged out of the step, however, it may also be recycled as it is as at least a part of water used in the first extraction step and/or the second extraction step, or unnecessary components may be removed before the recycling. Recycling of the ninth fraction is preferable since the water discharge amount as the whole purification process of crude dihydroxybenzene is reduced.

Feeding of the seventh fraction obtained in the second extraction step to the entrance of the first extraction step means that the seventh fraction obtained in the second extraction step is added as at least a part of a supply source of water to be added in the first extraction step, and thus, dihydroxybenzene contained in the seventh fraction shall be returned simultaneously to the first extraction step.

Since an independent distillation tower for recovery is not needed, the recovery step is preferably a step for feeding the seventh fraction obtained in the second extraction step to the entrance of the first extraction step, from the standpoint of suppressing equipment cost.

The maximum feature of the present invention is use of the first extraction step and the second extraction step in combination. By thus using the first extraction step and the second extraction step in combination, isopropenylphenol and hydroxyacetophenone can be removed with high efficiency from crude dihydroxybenzene. The present inventors have found that if an aqueous solution containing hydroxyacetophenone and dihydroxybenzene is subjected to extraction by allowing it to contact with an extraction solvent, the removal ratio of hydroxyacetophenone into the extraction solvent is influenced by the concentration of dihydroxybenzene contained in the aqueous solution. That is, it has been found that when the concentration of dihydroxybenzene contained in the aqueous solution is lower, the removal ratio of hydroxyacetophenone into the extraction solvent is higher.

If extraction is carried out only for one solution prepared by adding water to crude dihydroxybenzene, not according to the present invention, dihydroxybenzene having highly enhanced purity cannot be obtained efficiently, and for obtaining dihydroxybenzene having highly enhanced purity equivalent to that in the present invention, the amount of water to be removed in a distillation step increases remarkably, the scale of a distillation tower becomes large, and the quantity of heating energy used for dehydration increases, leading to poor efficiency.

In the present invention, it is preferable that the concentration ($C_A$) of dihydroxybenzene in the dihydroxybenzene aqueous solution A in the first extraction step is set at high level. By thus setting the concentration, a dihydroxybenzene aqueous solution (first fraction) is obtained in which most of isopropenylphenol is separated and removed into the extraction solvent (1) side, while hydroxyacetophenone is not removed sufficiently. Since the dihydroxybenzene concentration is high in subjecting this fraction to distillation as the former stage in the distillation step, the amount of water (third fraction) to be distilled and removed by distillation as the former stage may be small, the heating energy quantity can be reduced, and a relatively small scale distillation tower can be used in this step.

By setting the second extraction step, it is possible to suppress excess concentration of a heavy material of dihydroxyacetophenone (sixth fraction) containing concentrated hydroxyacetophenone obtained from around the tower bottom and to perform operation so as to give large content of dihydroxybenzene, in distillation as the latter stage. In the present invention, the concentration of hydroxyacetophenone in this fraction is usually 5 to 12 wt %, and dihydroxybenzene is contained in an amount of usually 70 to 95 wt %. If this fraction is not subjected to the second extraction step, loss of dihydroxybenzene is generated, leading to poor economy. In the second extraction step, it is preferable that the concentration of dihydroxybenzene in the dihydroxybenzene aqueous solution is set at a lower level than in the first extraction step.

Here, if water is added to dihydroxybenzene containing concentrated hydroxyacetophenone like the sixth fraction to give an aqueous solution having a low dihydroxybenzene concentration, then, an extraction solvent is added and an extraction operation is carried out, hydroxyacetophenone can be surprisingly removed more efficiently by far than in conventional technologies. If necessary, the resultant aqueous phase (seventh fraction) can be subjected to distillation to purify dihydroxybenzene and the dihydroxybenzene can be recovered as a product.

In the present invention, it is more preferable that the concentration ($C_A$) of dihydroxybenzene in the dihydroxybenzene aqueous solution A is 40 to 70 wt %, and the concentration ($C_B$) of dihydroxybenzene in the dihydroxybenzene aqueous solution B is 5 to 30 wt %.

When dihydroxybenzene is resorcin, the present invention is preferable from the standpoint of industrial application. Resorcin is principally used as a main raw material of an adhesive.

When dihydroxybenzene is hydroquinone, the present invention is preferable from the standpoint of industrial application. Hydroquinone is principally used as a reducing agent, polymerization inhibitor, rubber antioxidant, medicine raw material or the like.

When the concentration of isopropenylphenol in crude dihydroxybenzene is 0.1 to 20 wt % and the concentration of hydroxyacetophenone in crude dihydroxybenzene is 0.1 to 10 wt %, the present invention is particularly effective. When the method of the present invention is not used in such purification of crude dihydroxybenzene, the problems as previously described occur.

When the extraction solvent in the first extraction step and the second extraction step is toluene, the present invention is particularly preferable from the standpoint of not only extraction efficiency and liquid separation performance but also easy availability of the extraction solvent.

Further, the present invention relates to a production method of dihydroxybenzene comprising the following steps wherein the following purification step uses the above-described purification method of dihydroxybenzene:

oxidation step: diisopropylbenzene is oxidized to obtain an oxidized oil containing diisopropylbenzene dihydroperoxide, decomposition step: the oxidized oil obtained in the oxidation step is decomposed in the presence of an acidic catalyst to obtain a decomposition reaction solution containing dihydroxybenzene, purification step: the decomposition reaction solution obtained in the decomposition step is purified to obtain purified dihydroxybenzene.

Furthermore, it is preferable, from the standpoint of efficient purification, to previously separate light components (for example, acetone, etc.) and heavy components (compounds obtained by polymerization of dihydroxybenzene, isopropenylphenol and the like) contained in the decomposition reaction solution each by a separating operation such as distillation and the like, at any position connecting the decomposition step and the purification step described above.

EXAMPLES

The present invention will be illustrated specifically by examples.

Figure 1:
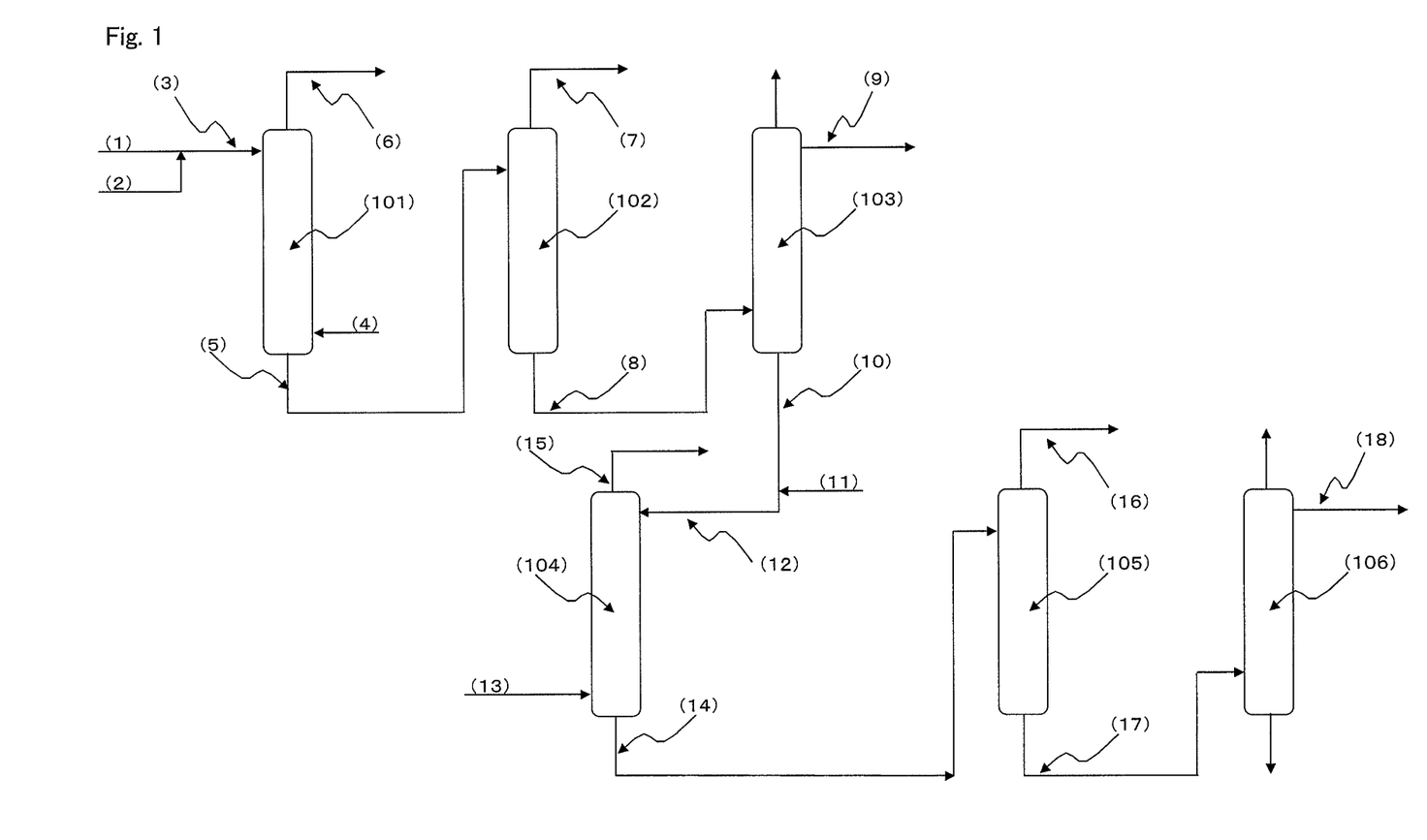
FIG. 1 is a schematic view of the flow of Example 1.

Example 1 (See, FIG. 1)

This shows a purification flow of crude dihydroxybenzene adopting the present invention and a brief summary thereof.
(I) Reaction Step Benzene and propylene are reacted to give m-diisopropylbenzene, then, m-diisopropylbenzene is oxidized to give m-diisopropylbenzene hydroperoxide, and m-diisopropylbenzene hydroperoxide is acid-decomposed in the presence of an acidic catalyst to give a reaction solution containing resorcin and acetone, then, it is subjected to distillation to remove light compounds such as acetone and the like, obtaining resorcin (m-dihydroxybenzene) containing m-isopropenylphenol and m-hydroxyacetophenone (hereinafter, referred to as "crude resorcin").
(II) Purification Step In the first extraction step, water (2) is added to crude resorcin (1) obtained in the reaction step (I) to prepare a ca. 53 wt % resorcin aqueous solution A (3), the solution is fed to a position near the tower head of a extraction tower (101), and toluene (4) as an extraction solvent (1) is fed in an amount of about 0.5 to 0.8-fold of the weight of the aqueous solution A to a position near the tower bottom of the extraction tower (101) and the solution is subjected to extraction by allowing it to contact with the solvent, to be separated into a first fraction (5) containing resorcin, m-hydroxyacetophenone and water and a second fraction (6) containing m-isopropenylphenol and toluene. In this case, the first fraction (5) is obtained from around the tower bottom of the extraction tower and the second fraction (6) is obtained from around the tower head of the extraction tower.

In the distillation step, first, the first fraction (5) obtained in the first extraction step is subjected to former stage distillation, to be separated into a third fraction (7) containing water and a fourth fraction (8) containing resorcin and m-hydroxyacetophenone.

In the former stage distillation, a packed distillation tower (102) is used. The third fraction (7) is obtained from around the tower head of the distillation tower (102) and the fourth fraction (8) is obtained from around the tower bottom.

Then, the fourth fraction (8) is subjected to latter stage distillation, to be separated into a fifth fraction (9) as purified resorcin and a sixth fraction (10) of resorcin containing m-hydroxyacetophenone.

In the latter stage distillation, a packed distillation tower (103) is used. The fifth fraction (9) is obtained from around the tower head of the distillation tower (103) and the sixth fraction (10) is obtained from around the tower bottom. The weight of the fifth fraction (9) is in the range of 0.7 to 0.95-fold of the weight of the fourth fraction (8).

In the second extraction step, water (11) is added to the sixth fraction (10) to prepare a ca. 15 wt % resorcin aqueous solution B (12), the solution is fed to a position near the tower head of a distillation tower (104), and toluene (13) as an extraction solvent (2) is fed in an amount of about 0.9 to 1.2-fold of the weight of the aqueous solution B to a position near the tower bottom of the extraction tower (104) and the solution is subjected to extraction by allowing it to contact with the solvent, to be separated into a seventh fraction (14) containing resorcin and water and an eighth fraction (15) containing m-hydroxyacetophenone and toluene. In this case, the seventh fraction (14) is obtained from around the tower bottom of the extraction tower and the eighth fraction (15) is obtained from around the tower head of the extraction tower.

In the recovery step, first, the seventh fraction (14) obtained in the second extraction step is subjected to former stage distillation, to be separated into a ninth fraction (16) containing water and a tenth fraction (17) containing dihydroxybenzene and hydroxyacetophenone.

In the former stage distillation, a packed distillation tower (105) is used. The ninth fraction (16) is obtained from around the tower head of a distillation tower (105) and the tenth fraction (17) is obtained from around the tower bottom. Then, the tenth fraction (17) is subjected to latter stage distillation, and dihydroxybenzene (18) is purified and recovered. In the latter stage distillation, a packed distillation tower (106) is used. Dihydroxybenzene (18) to be recovered is obtained from around the tower head of a distillation tower (106).

Figure 2:
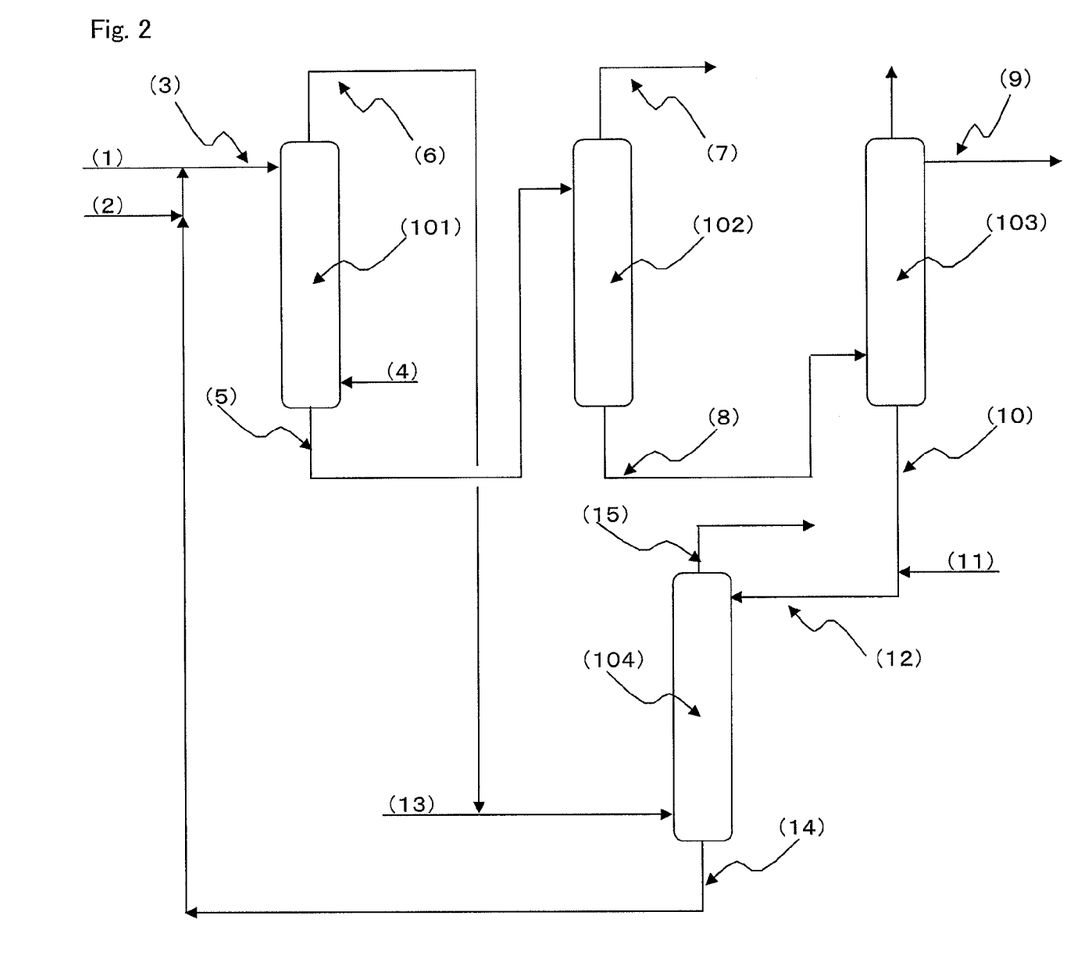
FIG. 2 is a schematic view of the flow of Example 2.

Example 2 (See, FIG. 2)

This shows the same purification flow of crude dihydroxybenzene and the same brief summary as in Example 1, excepting that, in the recovery step, an independent distillation tower is not installed and water and an extraction solvent are recycled in the step.

In the first extraction step, to the crude resorcin (1) obtained in the reaction step (I) of Example 1 is added the seventh fraction (14) obtained in the second extraction step, and if necessary, additional water (2) is added to prepare a ca. 53 wt % resorcin aqueous solution A (3), the solution is fed to a position near the tower head of the extraction tower (101), and toluene (4) as an extraction solvent (1) is fed in an amount of about 0.5 to 0.8-fold of the weight of the aqueous solution A to a position near the tower bottom of the extraction tower (101) and the solution is subjected to extraction by allowing it to contact with the solvent, to be separated into a first fraction (5) containing resorcin, m-hydroxyacetophenone and water and a second fraction (6) containing m-isopropenylphenol and toluene. In this case, the first fraction (5) is obtained from around the tower bottom of the extraction tower and the second fraction (6) is obtained from around the tower head of the extraction tower.

In the distillation step, first, the first fraction (5) obtained in the first extraction step is subjected to former stage distillation, to be separated into a third fraction (7) containing water and a fourth fraction (8) containing resorcin and m-hydroxyacetophenone.

In the former stage distillation, a packed distillation tower (102) is used. The third fraction (7) is obtained from around the tower head of the distillation tower (102) and the fourth fraction (8) is obtained from around the tower bottom.

Then, the fourth fraction (8) is subjected to latter stage distillation, to be separated into a fifth fraction (9) as purified resorcin and a sixth fraction (10) of resorcin containing m-hydroxyacetophenone.

In the latter stage distillation, a packed distillation tower (103) is used. The fifth fraction (9) is obtained from around the tower head of the distillation tower (103) and the sixth fraction (10) is obtained from around the tower bottom. The weight of the fifth fraction (9) is in the range of 0.7 to 0.95-fold of the weight of the fourth fraction (8).

In the second extraction step, water (11) is added to the sixth fraction (10) to prepare a ca. 15.0 wt % resorcin aqueous solution B (12), the solution is fed to a position near the tower head of a distillation tower (104), and the second fraction (6) obtained in the first extraction step is fed as an extraction solvent (2) to a position near the tower bottom of the extraction tower (104) and the solution is subjected to extraction by allowing it to contact with the solvent, to be separated into a seventh fraction (14) containing resorcin and water and an eighth fraction (15) containing m-hydroxyacetophenone and toluene. In this case, the seventh fraction (14) is obtained from around the tower bottom of the extraction tower and the eighth fraction (15) is obtained from around the tower head of the extraction tower.

In the recovery step, the seventh fraction (14) obtained in the second extraction step is used as water to be used in the first extraction step, and dihydroxybenzene contained in this fraction is simultaneously recovered into the first extraction step.

By this, equipment cost can be suppressed since an independent distillation tower is not needed for recovery. It also becomes possible to efficiently recycle water and the extraction solvent.

Figure 3:
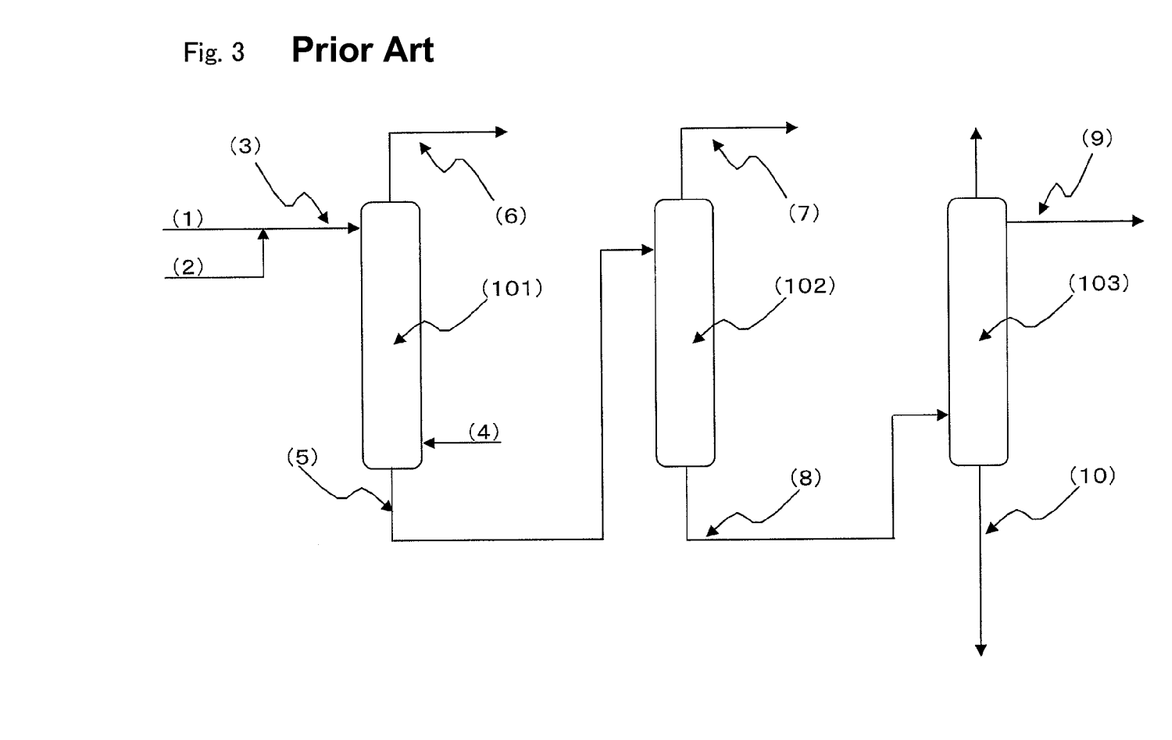
FIG. 3 is a schematic view of the flow of Comparative Examples 1 and 3.

Comparative Example 1 (See, FIG. 3)

This shows a conventional typical purification flow of crude dihydroxybenzene and a brief summary thereof.

The second extraction step and the recovery step are not utilized, not according to the present invention.

In the first extraction step, to the crude resorcin (1) obtained in the reaction step (1) of Example 1 is added water (2) to prepare a ca. 53 wt % resorcin aqueous solution A (3), the solution is fed to a position near the tower head of the distillation tower (101), and toluene (4) as an extraction solvent is fed in an amount of about 0.5 to 0.8-fold of the weight of the aqueous solution A to a position near the tower bottom of the extraction tower (101) and the solution is subjected to extraction by allowing it to contact with the solvent, to be separated into a first fraction (5) containing resorcin and water and a second fraction (6) containing m-isopropenylphenol, m-hydroxyacetophenone and toluene. In this case, the first fraction (5) is obtained from around the tower bottom of the extraction tower and the second fraction (6) is obtained from around the tower head of the extraction tower.

In the distillation step, first, the first fraction (5) obtained in the first extraction step is subjected to former stage distillation, to be separated into a third fraction (7) containing water and a fourth fraction (8) containing resorcin and m-hydroxyacetophenone.

In the former stage distillation, a packed distillation tower (102) is used. The third fraction (7) is obtained from around the tower head of the distillation tower (102) and the fourth fraction (8) is obtained from around the tower bottom.

Then, the fourth fraction (8) is subjected to latter stage distillation, to be separated into a fifth fraction (9) as purified resorcin and a sixth fraction (10) of resorcin containing m-hydroxyacetophenone.

In the latter stage distillation, a packed distillation tower (103) is used. The fifth fraction (9) is obtained from around the tower head of the distillation tower (103) and the sixth fraction (10) is obtained from around the tower bottom. The weight of the fifth fraction (9) is in the range of 0.7 to 0.95-fold of the weight of the fourth fraction (8).

According to this method, resorcin contained in the sixth fraction (10) is lost together with m-hydroxyacetophenone, it being impermissible.

Figure 4:
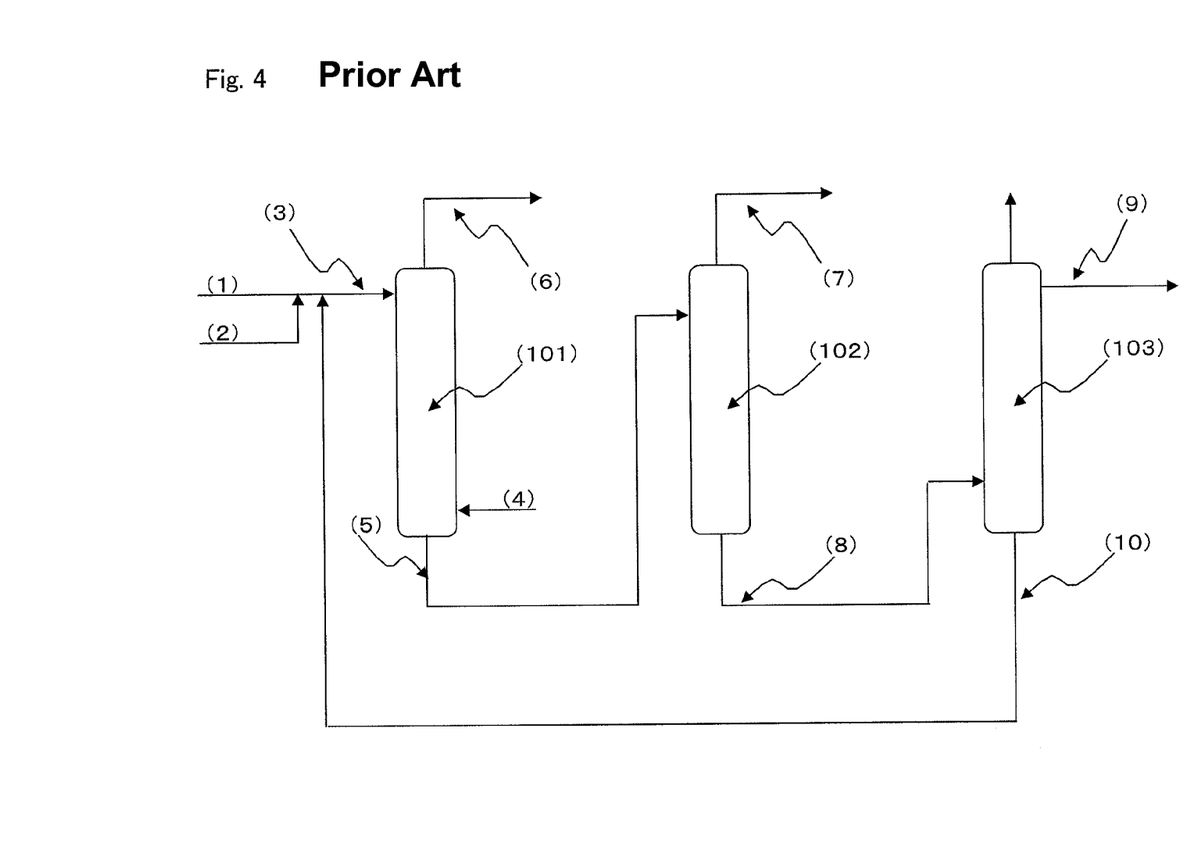
FIG. 4 is a schematic view of the flow of Comparative Example 2.

Comparative Example 2 (See, FIG. 4)

This shows a brief summary of the same conventional purification method of crude dihydroxybenzene as in Comparative Example 1, excepting that the sixth fraction (10) is not subjected to the second extraction step and recycled into the first extraction step.

According to this method, there is no means for efficiently extracting m-hydroxyacetophenone out of the step, and the concentration of m-hydroxyacetophenone in purified resorcin of the fifth fraction (9) increases.

Comparative Example 3 (See, FIG. 3)

This shows a brief summary of the same conventional purification method of crude dihydroxybenzene as in Comparative Example 1, excepting that the concentration A of the resorcin aqueous solution in the first extraction step is about 15 wt %.

In the first extraction step, to the crude resorcin (1) obtained in the reaction step (1) of Example 1 is added water (2) to prepare a ca. 15 wt % resorcin aqueous solution A (3), the solution is fed to a position near the tower head of the extraction tower (101), and toluene (4) as an extraction solvent is fed in an amount of about 0.5 to 0.8-fold of the weight of the aqueous solution A to a position near the tower bottom of the extraction tower (101) and the solution is subjected to extraction by allowing it to contact with the solvent, to be separated into a first fraction (5) containing resorcin, water, and m-hydroxyacetophenone not extracted into toluene, and a second fraction (6) containing m-isopropenylphenol, m-hydroxyacetophenone and toluene. In this case, the first fraction (5) is obtained from around the tower bottom of the extraction tower and the second fraction (6) is obtained from around the tower head of the extraction tower.

In the distillation step, first, the first fraction (5) obtained in the first extraction step is subjected to former stage distillation, to be separated into a third fraction (7) containing water and a fourth fraction (8) containing resorcin and m-hydroxyacetophenone.

In the former stage distillation, a packed distillation tower (102) is used. The third fraction (7) is obtained from around the tower head of the distillation tower (102) and the fourth fraction (8) is obtained from around the tower bottom.

Then, the fourth fraction (8) is subjected to latter stage distillation, to be separated into a fifth fraction (9) as purified resorcin and a sixth fraction (10) of resorcin containing m-hydroxyacetophenone.

In the latter stage distillation, a packed distillation tower (103) is used. The fifth fraction (9) is obtained from around the tower head of the distillation tower (103) and the sixth fraction (10) is obtained from around the tower bottom.

According to this method, since a larger amount of m-hydroxyacetophenone than in Comparative Example 1 can be removed in the first extraction step among m-hydroxyacetophenone contained in crude resorcin (1), the amount to be discharged out of the system from the sixth fraction (10) may be small and loss of purified resorcin as a product can be suppressed, however, since the amount of water to be used in the first extraction step increases significantly as compared with Examples 1 and 2, the quantity of heating energy for removing water in the distillation step increases, and the scale of the distillation tower in this step becomes larger.

Example 3

(I) Reaction Step

As raw materials, benzene and propylene were reacted to give m-diisopropylbenzene, the m-diisopropylbenzene was oxidized to give m-diisopropylbenzene hydroperoxide, and the m-diisopropylbenzene hydroperoxide was acid-decomposed in the presence of an acidic catalyst to give resorcin and acetone, the reaction solution obtained by this method was subjected to former distillation to remove light compounds such as acetone and the like, obtaining crude resorcin (m-isopropenylphenol concentration: 1.7 wt %, m-hydroxyacetophenone concentration: 0.2 wt %).

(II) Purification Step

As the first extraction step, water was added to crude resorcin to obtain an aqueous solution A having a resorcin concentration of 53 wt %, then, the solution was subjected to extraction by allowing it to contact with toluene as an extraction solvent (1), to be separated into a first fraction containing resorcin, m-hydroxyacetophenone and water and a second fraction containing m-isopropenylphenol and toluene.

A solution composed of crude resorcin and water was fed from a position near the tower head of the distillation tower (about 100 parts by weight per hour), and toluene as an extraction solvent was fed from a position near the tower bottom (about 63.6 parts by weight per hour), and both components were allowed to contact in the distillation tower and extracted therein.

By extraction, a first fraction containing resorcin, m-hydroxyacetophenone and water (about 101.8 parts by weight per hour) and a second fraction containing m-isopropenylphenol and toluene (about 61.8 parts by weight per hour) were obtained. The first fraction was obtained from around the tower bottom of the distillation tower and the second fraction was obtained from around the tower heat of the distillation tower.

The composition of the first fraction contains 50 wt % of resorcin and 0.2 wt % of m-hydroxyacetophenone, and the composition of the second fraction contained 2.6 wt % of m-isopropenylphenol.

As the distillation step, first, the first fraction obtained in the first extraction step was subjected to former stage distillation, to be separated into a third fraction containing water and a fourth fraction containing resorcin and m-hydroxyacetophenone.

In the former stage distillation, a packed distillation tower was used. The third fraction containing water was obtained from around the tower head of the distillation tower (about 50.9 parts by weight per hour) and the fourth fraction containing resorcin and m-hydroxyacetophenone was obtained from around the tower bottom (about 50.9 parts by weight per hour).

Then, the fourth fraction was subjected to latter stage distillation, to be separated into a fifth fraction containing purified resorcin and a sixth fraction of resorcin containing m-hydroxyacetophenone.

In the latter stage distillation, a packed distillation tower was used. The fifth fraction containing purified resorcin was obtained from around the tower head of the distillation tower (about 47.3 parts by weight per hour) and the sixth fraction of resorcin containing m-hydroxyacetophenone was obtained from around the tower bottom (about 3.6 parts by weight per hour). The concentration of m-hydroxyacetophenone in the fifth fraction was 49 wtppm. The concentration of m-hydroxyacetophenone in the sixth fraction was 7.5 wt %.

In the second extraction step, water was added to the sixth fraction obtained in the rectification step to obtain a solution having a resorcin concentration of 15 wt %, then, the solution was subjected to extraction by allowing it to contact with toluene as an extraction solvent (2), to be separated into a seventh fraction containing resorcin and water and an eighth fraction containing m-hydroxyacetophenone and toluene, and the seventh fraction was fed to the entrance of the first extraction step.

A solution obtained by adding water to the sixth fraction was fed from around the tower head of the distillation tower (about 54.5 parts by weight per hour), and toluene as an extraction solvent was fed from around the tower bottom (about 61.8 parts by weight per hour), and both components were allowed to contact in the extraction tower and extracted therein.

By extraction, a seventh fraction containing resorcin and water was obtained from around the tower bottom of the distillation tower (about 54.5 parts by weight per hour), and an eighth fraction containing m-hydroxyacetophenone and toluene was obtained from around the tower head (about 61.8 parts by weight per hour). In the seventh fraction, the resorcin concentration was 15 wt %, and in the eighth fraction, the m-hydroxyacetophenone concentration was 0.2 wt %.

Comparative Example 4 (See, FIG. 3)

Extraction was performed only for one aqueous solution A obtained by adding water to crude resorcin, not according to the present invention. That was, the first extraction step of the present invention (here, a solution having a resorcin concentration of 53 wt % obtained by adding water to crude resorcin was used), a dehydration step and a rectification step were used.

Based on the results in Example 3 and Comparative Example 4, the effects of the presence and absence of 2-stage extraction using the first extraction step and the second extraction step in combination, the feather of the present invention, were compared and the results are shown in Table 1.

TABLE 1

|  | Example 3 | Comparative Example 4 |
| --- | --- | --- |
| Resorcin aqueous solution concentration (wt %) in first extraction step | 53 | 53 |
| Resorcin aqueous solution concentration (wt %) in second extraction step | 15 | Not carried out |
| Impurity concentration (wtppm) in product resorcin (fifth fraction) |  |  |
| m-isopropenylphenol | 18 | 37 |
| m-hydroxyacetophenone | 49 | 78 |

Example 4

Figure 5:
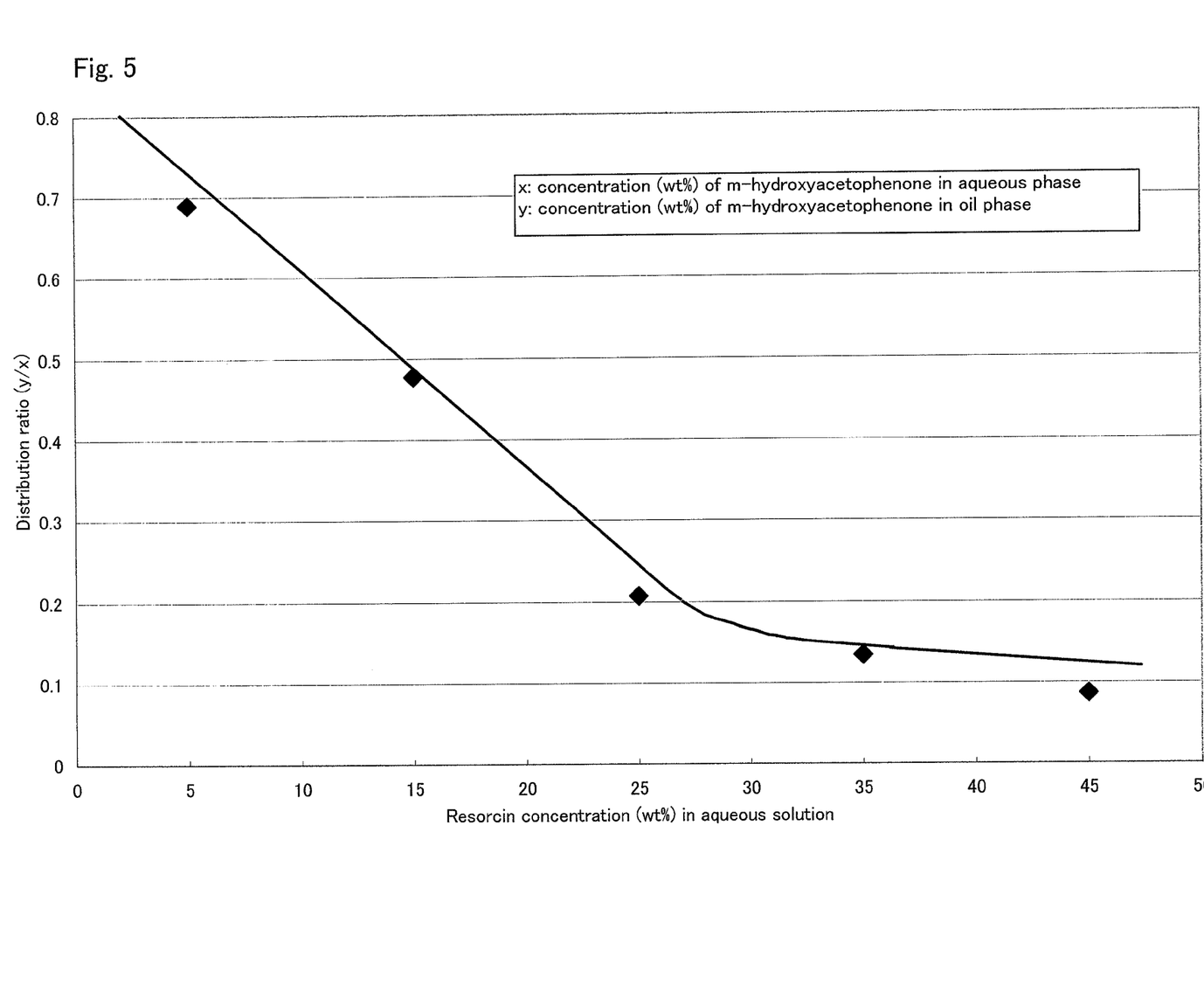
FIG. 5 is a view showing the resorcin concentration in an aqueous solution and the distribution ratio of hydroxyacetophenone.

An aqueous solution containing m-hydroxyacetophenone and resorcin (hereinafter, referred to as "resorcin aqueous solution" in some cases) was subjected to extraction by allowing it to contact with toluene, and the ratio of the concentration (wt %) (x) of m-hydroxyacetophenone in the aqueous phase to the concentration (wt %) (y) of m-hydroxyacetophenone in the toluene phase was measured, and the distribution ratio (y/x) is shown in FIG. 5. Larger distribution ratio (y/x) denotes easier transfer of m-hydroxyacetophenone from the aqueous phase to the toluene phase.

FIG. 5 teaches that, in the case of a resorcin aqueous solution having a resorcin concentration of 30 wt % or less, when the resorcin concentration in the resorcin aqueous solution is lower, the distribution ratio (y/x) increases linearly, and a larger amount of m-hydroxyacetophenone is contained in the toluene phase. This teaches that when a region having a higher resorcin aqueous solution concentration is adopted in the first extraction step and a region having a lower resorcin aqueous solution concentration is adopted in the second extraction step, in the present invention, m-hydroxyacetophenone can be removed more efficiently into the toluene phase in the second extraction step than in the first extraction step.

Industrial Applicability.

The present invention can be utilized for an extremely excellent purification method of dihydroxybenzene, which is capable of efficiently obtaining highly purified dihydroxybenzene.

The invention claimed is:

1. A purification method of dihydroxybenzene comprising the following steps, for obtaining purified dihydroxybenzene from crude dihydroxybenzene containing at least isopropenylphenol and hydroxyacetophenone as impurities:

first extraction step: water is added to crude dihydroxybenzene to prepare a dihydroxybenzene aqueous solution A, then, the solution is subjected to extraction by allowing it to contact with an extraction solvent (1), to be separated into a first fraction containing dihydroxybenzene, hydroxyacetophenone and water and a second fraction containing isopropenylphenol and the extraction solvent (1), distillation step: the first fraction obtained in the first extraction step is subjected to distillation, to be separated into a third fraction containing water and a fourth fraction containing dihydroxybenzene and hydroxyacetophenone, then, the fourth fraction is subjected to distillation, to be separated into a fifth fraction as purified dihydroxybenzene and a sixth fraction as dihydroxybenzene containing concentrated hydroxyacetophenone, second extraction step: water is added to the sixth fraction obtained in the distillation step to prepare a dihydroxybenzene aqueous solution B, then, the solution is subjected to extraction by allowing it to contact with an extraction solvent (2), to be separated into a seventh fraction containing dihydroxybenzene, hydroxyacetophenone, and water and an eighth fraction containing hydroxyacetophenone and the extraction solvent (2), recovery step: dihydroxybenzene is recovered from the seventh fraction obtained in the second extraction step or the seventh fraction obtained in the second extraction step is fed to the entrance of the first extraction step.

2. The purification method according to claim 1, wherein the concentrations of dihydroxybenzene in the dihydroxybenzene aqueous solution in the first extraction step and the second extraction step satisfy the following formula (1):

$$CA > CB \quad (1)$$

(wherein, CA represents the concentration [wt %] of dihydroxybenzene in the dihydroxybenzene aqueous solution A, and CB represents the concentration [wt %] of dihydroxybenzene in the dihydroxybenzene aqueous solution B).

3. The purification method according to claim 1, wherein the recovery step is a step described below:

recovery step: the seventh fraction obtained in the second extraction step is subjected to distillation, to be separated into a ninth fraction containing water and a tenth fraction containing dihydroxybenzene and hydroxyacetophenone, then, the tenth fraction is subjected to distillation, and dihydroxybenzene is recovered.

4. The purification method according to claim 1, wherein dihydroxybenzene is resorcin.

5. The purification method according to claim 1, wherein dihydroxybenzene is hydroquinone.

6. The purification method according to claim 1, wherein the concentration of isopropenylphenol in crude dihydroxybenzene is 0.1 to 20 wt %, and the concentration of hydroxyacetophenone is 0.1 to 10wt %.

7. The purification method according to claim 1, wherein the extraction solvent (1) and the extraction solvent (2) are toluene.

8. A production method of dihydroxybenzene comprising the following steps wherein the following purification step uses the purification method of dihydroxybenzene according to claim 1, oxidation step: diisopropylbenzene is oxidized to obtain an oxidized oil containing diisopropylbenzene dihydroperoxide, decomposition step: the oxidized oil obtained in the oxidation step is decomposed in the presence of an acidic catalyst to obtain a decomposition reaction solution containing dihydroxybenzene, purification step: the decomposition reaction solution obtained in the decomposition step is purified to obtain purified dihydroxybenzene.

\* \* \* \* \*